| United States Patent [19] | [11] Patent Number: 4,562,010 |
| Goliasch et al. | [45] Date of Patent: Dec. 31, 1985 |

[54] PROCESS FOR THE PREPARATION OF BENZOIC ANHYDRIDE

[75] Inventors: Karl Goliasch, Bergisch-Gladbach; Herbert Müller, Cologne; Heinrich Pelster, Odenthal, all of Fed. Rep. of Germany

[73] Assignee: Bayer Aktiengesellschaft, Leverkusen, Fed. Rep. of Germany

[21] Appl. No.: 703,373

[22] Filed: Feb. 20, 1985

Related U.S. Application Data

[63] Continuation of Ser. No. 223,969, Jan. 12, 1981, abandoned, which is a continuation of Ser. No. 65,822, Aug. 13, 1979, abandoned.

[30] Foreign Application Priority Data

Aug. 28, 1978 [DE] Fed. Rep. of Germany ....... 2837457

[51] Int. Cl.$^4$ .............................................. C07C 51/56
[52] U.S. Cl. .................................................... 260/546
[58] Field of Search ......................................... 260/546

[56] References Cited

FOREIGN PATENT DOCUMENTS 0280373 11/1927 United Kingdom ................ 260/546

*Primary Examiner*—Bernard Helfin
*Attorney, Agent, or Firm*—Sprung Horn Kramer & Woods

[57] ABSTRACT

A process for preparing benzoic anhydride which comprises contacting benzotrichloride with benzoic acid in a molar ratio of 1:2–3 at a temperature in the range of 100°–200° C.

2 Claims, 1 Drawing Figure

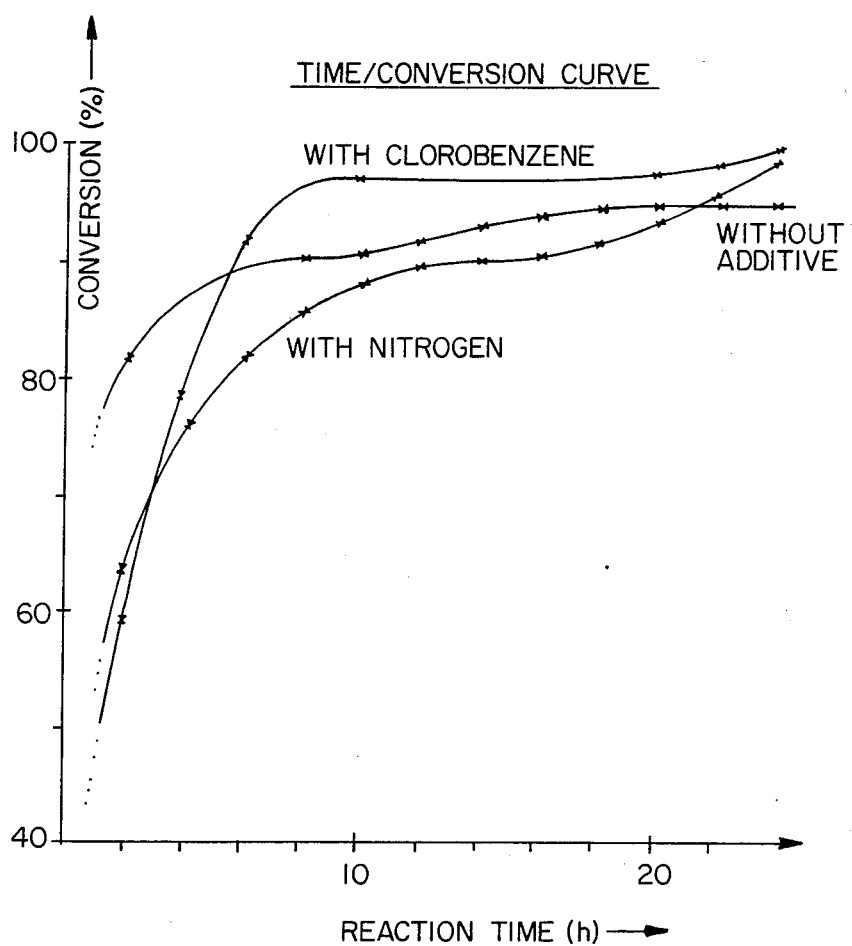

PROCESS FOR THE PREPARATION OF BENZOIC ANHYDRIDE

This is a continuation of application Ser. No. 223,969, filed Jan. 12, 1981, which is a continuation of Ser. No. 65,822, filed Aug. 13, 1979, and both now abandoned.

The invention relates to a process for the preparation of benzoic anhydride from benzotrichloride and benzoic acid.

It is known to prepare benzoic anhydride by reacting benzotrichloride with sodium benzoate at temperatures from 160° to 170° C. (German Patent Specification No. 368,340, Example 4).

This procedure has the disadvantage that, after the reaction, benzoic anhydride must be separated off from the salts formed. Separating the benzoic anhydride off from the salts requires a considerable technical effort, since the salts are obtained in a finely divided form which is difficult to filter.

Furthermore, it is not very economical to separate off the benzoic anhydride by distillation, since the distillation is carried out in vacuo at temperatures of about 200° C. and, because of the salts which the distillation bottom product contains and which cause corrosion, must be carried out in special apparatuses.

Extraction of the reaction mixture to isolate benzoic anhydride is similarly not very economical, since additional apparatuses and relatively large amounts of solvents are required for this extraction. Moreover, the extract must be separated off from the salts, whereupon the abovementioned problems result.

A process has now been found for the preparation of benzoic anhydride, which is characterised in that benzotrichloride is reacted with benzoic acid in a molar ratio of about 1:2 to about 1:3 at temperatures in the range from about 100° to about 200° C.

In a preferred embodiment of the process according to the invention, the molar ratio of benzotrichloride to benzoic acid is about 1:2.5. The reaction takes place at reaction temperatures in the range from about 140° to about 180° C.

When the reaction has ended, the benzoic anhydride is separated off from benzoic acid which has still not reacted without trace and from benzotrichloride which has still not completely reacted, as well as from benzoyl chloride, which is formed in small amounts as a by-product, by incipient distillation at temperatures in the range from about 120° to 200° C., preferably 140° to 180° C., and under pressures in the range from about 10 to 200 mbars, preferably 20 to 100 mbars.

Benzoic anhydride thereby remains, in the pure form (purity $\geq$ 98%), as a high-boiling distillation residue in the distillation vessel. The entire distillate mixture separated off, consisting of benzoic acid, benzotrichloride and benzoyl chloride, is recycled and fed again into the starting reaction mixture, that is to say a new batch. In this manner, the components employed are reacted completely and a virtually quantitative yield of benzoic anhydride is achieved.

An inert gas can be passed into the reaction mixture to accelerate the reaction and to bring the conversion to completion. In general, the procedure in this case is to gradually increase the amount of inert gas during the period of introduction. The final amount of inert gas can thereby be about 2 to about 10 times, preferably 4 times to 8 times, the initial amount of inert gas. At the same time as passing in the inert gas, the reaction temperature is gradually increased from about 120° up to about 180° C.

Nitrogen is preferably used as the inert gas.

The amount of inert gas which is passed into the reaction mixture depends on the amount of starting materials and the dimensions of the reactor, and in general is about 1 to 10 m$^3$, preferably 3 to 8 m$^3$, per hour and per m$^3$ of reaction volume.

The same effect, that is to say acceleration of the reaction and completion of the conversion, can be achieved if, instead of passing in an inert gas, inert organic solvents are added to the reaction mixture. In this case, advantageously, the inert organic solvents are not added at the start of the reaction, but only after a conversion of about 60% has been achieved and the first vigorous evolution of hydrogen chloride has subsided. It is appropriate to add the inert organic solvent to the reaction mixture in several small portions or continuously, in a manner such that the reaction mixture is kept continuously under reflux whilst maintaining a bottom temperature of about 150° to about 180° C.

Possible inert, organic solvents are those which can be evaporated under the reaction conditions.

Examples of solvents which can be employed are aliphatic, cycloaliphatic, araliphatic or aromatic hydrocarbons which have up to 12 carbon atoms, preferably up to 8 carbon atoms, and are optionally monosubstituted or polysubstituted by halogen and/or by alkyl radicals with 1 to 10, preferably 1 to 8, carbon atoms.

Examples of halogens which may be mentioned are: fluorine, chlorine and bromine, preferably fluorine and chlorine.

Examples of optionally substituted aliphatic hydrocarbons which may be mentioned are: pentane, hexane, heptane, methylene chloride, chloroform, carbon tetrachloride, 1,2-dichloroethane, 1,1,1-trichloroethane, 1,1,2-trichloroethylene and 1,2-dichlorobutane, preferably hexane; examples which may be mentioned of optionally substituted cycloaliphatic hydrocarbons are: cyclohexane and methylcyclohexane, preferably cyclohexane; examples which may be mentioned of optionally substituted araliphatic hydrocarbons are: toluene, xylene, trimethylbenzene and ethylbenzene, preferably toluene; and examples which may be mentioned of optionally substituted aromatic hydrocarbons are: benzene, fluorobenzene, chlorobenzene, 1,2-dichlorobenzene and 1-chlorotoluene, preferably chlorobenzene.

Aliphatic or aromatic hydrocarbons, such as methylene chloride, chlorobenzene and dichlorobenzene, are preferably employed as the inert organic solvents in the process according to the invention.

The inert organic solvents can be added to the reaction mixture individually or as mixtures with one another. It is also possible to additionally pass an inert gas into the reaction mixture to which inert organic solvents have been added.

The amount of inert organic solvents added depends on the nature of the solvents and can easily be determined by preliminary experiments.

Acceleration of the reaction can also be achieved by applying a slight vacuum. In this case, the reaction is carried out under about 700 to 380 mm Hg, preferably 500 to 400 mm Hg.

The process according to the invention can be carried out either discontinuously or continuously.

BRIEF DESCRIPTION OF DRAWING

The accompanying drawing represents a time/conversion curve showing the effect of time of reaction on conversion when the process is carried out using chlorobenzene as solvent, without the use of an additive and using nitrogen gas as an inert gas sweep.

In a preferred embodiment of the process according to the invention, benzotrichloride is reacted with benzoic acid in a molar ratio of 1:2.5 in a stirred kettle, whilst stirring and heating to about 140° to 150° C. The rate of heating is chosen so that an essentially uniform evolution of hydrogen chloride, which becomes weaker towards the end of the reaction, takes place. When the first evolution of hydrogen chloride has subsided, nitrogen is passed into the reaction mixture. In general, the procedure in this case is to gradually increase the amount of nitrogen during the period of introduction. The final amount of nitrogen can be 2 to 10 times the initial amount of nitrogen.

When 2.5 mols of hydrogen chloride, relative to the benzotrichloride employed, have been liberated, the reaction is interrupted. The reaction mixture is then worked up by incipient distillation in vacuo under about 20 to 100 mbars and at about 140° to 180° C. The unreacted benzoic acid together with residual benzotrichloride and benzoyl chloride is thereby separated off from the benzoic anhydride, which remains in the pure form as the residue.

The benzoic anhydride prepared from benzotrichloride and benzoic acid by the process according to the invention is obtained, as the undistilled crude material, in high purity ($\geq 98\%$ pure) and in an almost colorless form. The yield is about 95% of theory (relative to benzotrichloride). The benzoic anhydride contains less than 1% of benzoic acid and less than 0.2% of benzoyl chloride (calculated from a content of saponifiable Cl of less than 0.05%).

The advantages of the process according to the invention are, above all, the almost quantitative conversion of the benzotrichloride to benzoic anhydride and the high purity with which the benzoic anhydride is obtained without prior distillation.

Furthermore, the use of expensive special apparatuses and the carrying out of expensive separation operations can be dispensed with in carrying out the process according to the invention, since the unreacted starting substances are separated off from the benzoic anhydride in the process according to the invention.

Benzoic anhydride is, for example, a valuable intermediate product for the preparation of benzoyl cyanide, which is formed, for example, by reaction with hydrocyanic acid and which is used for the preparation of plant protection agents (compare DE-OS (German Published Specification) No. 2,224,161).

The process according to the invention is described by the following examples, but without being restricted to these examples.

EXAMPLE 1

About 500 kg (4.10 kmols) of benzoic acid and about 320 kg (1.64 kmols) of benzotrichloride are reacted, by heating to 140° to 150° C., in an enamel stirred kettle which can be heated and cooled and has a capacity of 1 m$^3$ and suitable glass distillation equipment. The rate of heating per unit time is controlled according to the evolution of hydrogen chloride. The reaction takes about 5 hours. The hydrogen chloride escaping is passed to a suitable absorption unit for the preparation of hydrochloric acid.

To the following batch there is also added the distillate from the previous batch, consisting of about 200 to 300 kg of a mixture of about 10 to 30% of benzotrichloride, about 50 to 80% of benzoyl chloride and about 5 to 10% of benzoic acid. Benzoic acid and benzotrichloride are added to the new batch in amounts such that the molar ratio of the benzoic acid to benzotrichloride is about 1:2.5. It is assumed here that the Cl content of the distillate of the previous batch exists exclusively as benzotrichloride.

After a reaction time of 3 to 4 hours at about 140° C., the evolution of hydrochloride subsides. Nitrogen is now bubbled in via a dip tube. The amount of nitrogen is increased from initially about 1 m$^3$ per hour to 5 m$^3$ per hour in the course of 5 hours.

Most of the hydrogen chloride is liberated in the course of about 10 hours. The course of the reaction is followed analytically. The reaction is interrupted after at least 2.5 mols of HCl, relative to benzotrichloride employed, have been liberated.

After the reaction has been interrupted, the benzoic anhydride is separated off from benzoic acid which has still not completely reacted and benzotrichloride which also has still not completely reacted, as well as from benzoyl chloride, which is formed as a by-product, by distillation at temperatures in the ranges from 140° to 180° C. and under pressures in the range from 20 to 100 mbars. The benzoic anhydride thereby remains, in a pure form ($\geq 98\%$ pure), in the distillation vessel as a high-boiling distillation residue. The entire distillate mixture separated off consisting of benzoic acid, benzenetrichloride and benzoyl chloride, is, as described above, recycled and fed again into a new reaction batch.

After carrying out 16 batches in the manner described above, a total of 5,198 kg of benzotrichloride and 8,806 kg of benzoic acid has been consumed and 10,376 kg of benzoic anhydride have been obtained in a purity of $\geq 98\%$ as the distillation residue.

In this procedure, 844 kg of distillate (first runnings) were weighed out as the by-product, which, with a chloride content (based on pure benzotrichloride) of about 30%, corresponds to 465 kg of benzotrichloride and 379 kg of benzoic acid. With appropriate correction of the amounts employed, a yield of 95% of theory relative to benzotrichloride and 100% of theory relative to benzoic acid is calculated from these figures.

EXAMPLE 2

391 g (2 mols) of benzotrichloride and 610 g (5 mols) of benzoic acid were initially introduced into a 1 l three-necked flask with a stirrer, metering funnel and reflux condenser (set up on a suitable laboratory balance). In this experiment, the course of the conversion was followed on the basis of the weight loss caused by the evolution of hydrogen chloride. A weight loss of 182.5 g was rated as 100% conversion.

The following comparison experiments were carried out: (1) reaction without introduction of nitrogen; (2) reaction with introduction of nitrogen; and (3) reaction with addition of chlorobenzene (gradual addition, in portions, of a total of 193 g of chlorobenzene after a reaction time of 3 hours).

The time/conversion curves determined from the weight losses are shown in the accompanying figure.

The experiments show that, compared with passing in nitrogen, by adding chlorobenzene the reaction time can be shortened again and the conversions can be increased. Advantageously, in this case, the chlorobenzene is not already added before the start of the reaction, but only gradually in several portions after ⅔ of the conversion, so that the mixture continuously boils under reflux at a bottom temperature of about 180° C.

EXAMPLE 3

586.5 g (3 mols) of benzotrichloride and 722 g (6 mols) of benzoic acid were weighed out into a 2 l three-necked flask with a stirrer and reflux condenser and were heated to 150° C., during which splitting off of hydrogen chloride starts from about 110° C. After 5 hours, the mixture is heated to 180° C. and kept at this temperature for 3 hours. Thereafter, unreacted benzotrichloride and benzoic acid and the by-product benzoyl chloride are separated off by incipient distillation in vacuo (140°–180° C., 200–20 mbars) (960 g of distillate). 703.9 g of benzoic anhydride (98.2% pure, melting point: 39°–40° C.) remain as the distillation residue, that is to say the conversion is 77.8%.

On carrying out the experiment repeatedly, the distillate from the previous experiment in each case being added to the next batch, a virtually quantitative yield relative to benzoic acid is calculated.

What is claimed is:

1. A process for preparing benzoic anhydride which comprises contacting benzotrichloride with benzoic acid in a molar ratio of 1:2–3 at a temperature in the range of 100°–200° C., separating off from the reaction mixture benzoyl chloride formed as by-product, together with residual unreacted benzoic acid and/or residual unreacted benzotrichloride and adding them again to a starting reaction mixture, wherein the initial reaction of said benzotrichloride and benzoic acid is effected in the absence of an additive other than a solvent or an inert sweep gas.

2. A process according to claim 1 wherein said starting reaction mixture is one which is free of an additive other than a solvent or an inert gas or said benzoyl chloride by-product in admixture with said residual unreacted benzoic acid and/or said residual unreacted benzotrichloride.

* * * * *